United States Patent
Giet et al.

(12) 
(10) Patent No.: US 6,319,254 B1
(45) Date of Patent: Nov. 20, 2001

(54) COMPRESSION OSTEOSYNTHESIS SCREW, AND AN ANCILLATY DEVICE FOR USE THEREWITH

(75) Inventors: Jean-Christophe Alain Giet, Lyons (FR); Theo Jan Maria Knevels, Grimbergen (BE); Eric Stéphane Fourcault, Lyons (FR)

(73) Assignee: Newdeal, Vienne (FR)

( * ) Notice: Subject to any disclaimer, the term of this patent is extended or adjusted under 35 U.S.C. 154(b) by 0 days.

(21) Appl. No.: 09/553,860

(22) Filed: Apr. 21, 2000

(30) Foreign Application Priority Data

Apr. 22, 1999 (FR) .................................................. 99 05399

(51) Int. Cl.$^7$ .................................................. A61B 17/86
(52) U.S. Cl. ............................................. 606/73; 606/104
(58) Field of Search .................. 606/60, 65, 72, 606/73, 104; 411/178, 263, 307, 389, 397

(56) References Cited

U.S. PATENT DOCUMENTS

| 4,175,555 | * | 11/1979 | Herbert . | |
|---|---|---|---|---|
| 4,463,753 | * | 8/1984 | Gustilo . | |
| 4,640,271 | * | 2/1987 | Lower . | |
| 5,536,127 | * | 7/1996 | Pennig | 411/413 |
| 5,997,541 | * | 12/1999 | Schenk | 606/73 |
| 6,001,101 | * | 12/1999 | Augagneur et al. | 606/73 |

FOREIGN PATENT DOCUMENTS

| 2699065 | 6/1994 | (FR) . |
|---|---|---|
| 2728778 | 7/1996 | (FR) . |
| 2745709 | 9/1997 | (FR) . |
| 10-52439 | 2/1998 | (JP) . |
| WO 91/09572 | 7/1991 | (WO) . |

* cited by examiner

Primary Examiner—David O. Reip
(74) Attorney, Agent, or Firm—Millen, White, Zelano & Branigan

(57) ABSTRACT

An osteosynthesis screw comprising both a screw shank, having a thread with a distal zone and a proximal zone, and a screw head for threading on the screw shank and for co-operating with its proximal zone via internal tapping complementary to the thread of the shank is suitable for applying compression to bone fragments. The screw head also has an outside thread at a pitch that is smaller than the pitch of the screw shank, wherein the distal zone and the proximal zone are separated by a central zone shaped to be inactive during screwing so as to form a sliding zone for the bone fragments to be put into compression.

18 Claims, 3 Drawing Sheets

COMPRESSION OSTEOSYNTHESIS SCREW, AND AN ANCILLATY DEVICE FOR USE THEREWITH

FIELD OF THE INVENTION

The present invention relates to the technical field of bone surgery, and in particular to osteosynthesis appliances for bringing fractured bone fragments together, for putting them under compression, and then for uniting them, by means of screws, bolts, nails, metal plates, etc.

The present invention relates to a compression osteosynthesis screw for putting fractured bone fragments under compression, said screw comprising both a screw shank having a thread with a distal zone and a proximal zone, and also a screw head for threading on said screw shank and for co-operating with its proximal zone via internal tapping complementary to the thread of said screw shank, said screw head also having an outside thread at a pitch that is smaller than the pitch of the screw shank.

The present invention also relates to an ancillary device for use with a compression osteosynthesis screw.

BACKGROUND OF THE INVENTION

It is thus already known to unite bone fragments by means of a screw whose shank is pierced over its entire length and which has an outside thread over its entire length. The screw is associated with a separate screw head that has a through internal well so as to be capable of being threaded onto the screw shank. The internal well is provided with tapping complementary to the thread of the screw shank so as to be capable of co-operating therewith and of moving along the entire length of the thread so as to come into abutment in the proximal zone of the screw shank. The screw head also has an outside thread at a smaller pitch than the thread of the screw shank.

In general, such a device gives results that are satisfactory in terms of osteosynthesis treatment since, by screwing the screw shank through the bone fragments, it enables the bone fragments to be brought together, enabling the various bone fragments to be united by jointing at the line of fracture. That device also makes it possible to put the bone fragments under a small amount of compression because of the existence of a pitch differential between the outside screw thread on the screw head and the thread on the screw shank. The existence of a screw pitch differential at the outside thread of the screw head makes it possible, when the head begins to penetrate into a portion of bone, to urge the bone fragments towards one another, which implies putting them into compression. Such compression can also be increased slightly by rotating the head of the screw on its own, thereby making it possible to control or perceptibly increase the amount of compression.

Nevertheless, such a device suffers from drawbacks that put a limit on the amount of compression that can be applied to bone fragments because of the existence of the thread on the screw shank which opposes the application of compression because it is anchored directly in the bone fragments. In addition, the presence of the thread on the screw shank can give rise to bone trauma that is harmful for proper resorption of the fracture.

Other types of dual-pitch compression osteosynthesis screw also exist in the prior art, such screws not having an independent screw head and consequently enabling only a moderate amount of compression to be applied to the bone fragments that are to be united.

OBJECTS AND SUMMARY OF THE INVENTION

Consequently, the present invention provides a remedy to the various drawbacks mentioned above by providing a novel compression osteosynthesis screw that is easier to install and has the ability to apply increased compression to the bone fragments to be united.

Another object of the invention is to provide a novel compression osteosynthesis screw that is simple to manufacture, low in cost, and for which the risks of bone trauma are under control.

Another object of the invention is to provide a novel compression osteosynthesis screw having good mechanical strength while reducing the risks of resorption phenomena appearing.

Another object of the invention is to provide a novel ancillary device for use with a compression osteosynthesis screw which makes it possible during an operation, in reliable manner and in complete safety, to prevent the screw head from losing contact with its thread for engagement on the screw shank.

Upon further study of the specification and appended claims, further objects and advantages of this invention will become apparent to those skilled in the art.

The objects of the invention are achieved by means of an osteosynthesis screw for applying compression to bone fragments, the screw comprising both a screw shank having a thread with a distal zone and a proximal zone, and also a screw head for threading on said screw shank and for co-operating with its proximal zone via internal tapping complementary to the thread of said shank, said screw head also having an outside thread at a pitch that is smaller than the pitch of the screw shank, wherein the distal zone and the proximal zone are separated by a central zone shaped to be inactive during screwing so as to form a sliding zone for the bone fragments to be put into compression.

The objects of the invention are also achieved by means of an ancillary device for use with the osteosynthesis screw of the invention, the device comprising a first screwdriver designed for turning the screw shank and a second screwdriver designed for turning the screw head, the first screwdriver being engaged axially inside the second screwdriver so as to enable the screw shank and the screw head to be turned simultaneously, and being separable therefrom so as to enable the screw head to be turned individually, wherein the second screwdriver is provided at its working end portion with an internal setback designed to receive the collar of the screw shank in an abutment position against the end of the setback, said setback being of a depth such that when the collar comes into abutment against its end while the screw head is being turned, further turning thereof is automatically blocked before the last turn of the proximal thread has been reached so as to prevent the screw head from escaping from said proximal thread.

BRIEF DESCRIPTION OF THE DRAWINGS

Various other features and attendant advantages of the present invention will be more fully appreciated as the same becomes better understood when considered in conjunction with the accompanying drawings, in which like reference characters designate the same or similar parts throughout the several views, and wherein.

DETAILED DESCRIPTION OF THE DRAWINGS

Figure 1:
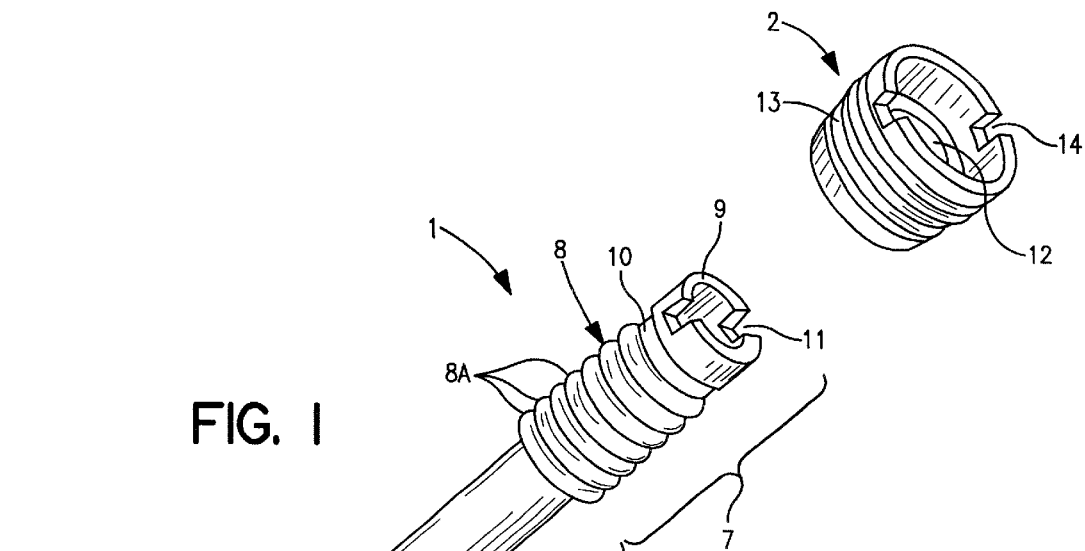
FIG. 1 is an exploded perspective view showing a compression osteosynthesis screw of the invention with a screw shank and a screw head that are separate.
Figure 2:
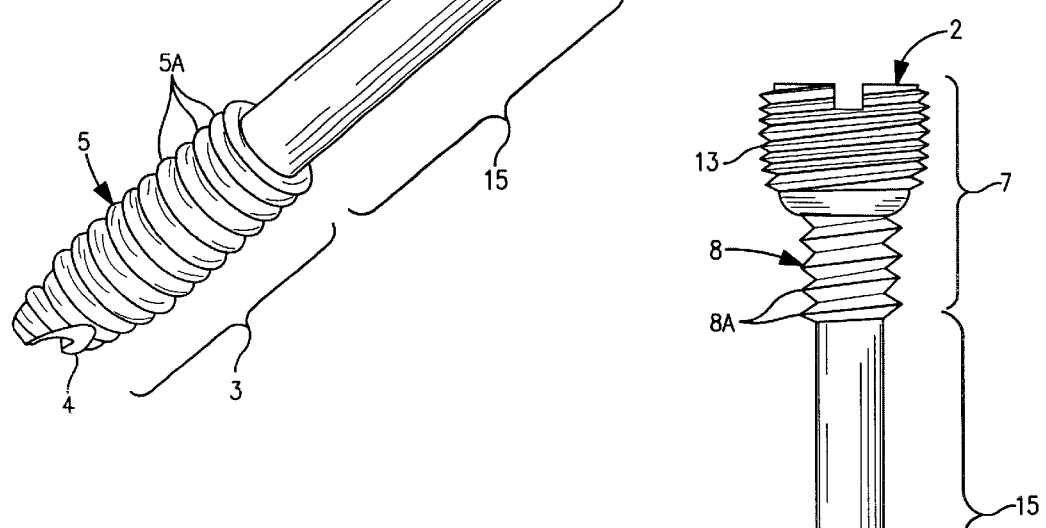
FIG. 2 is a side view of a compression osteosynthesis screw of the invention showing the screw head mounted in its abutment position on the screw shank.

FIGS. 1 and 2 are general views of a compression osteosynthesis screw of the invention. Such a screw is made up of two distinct elements that are designed to be assembled together and that comprise a screw shank 1 and a screw head 2. These two elements are made of specially treated metals selected for suitability for use in the field of surgery.

The screw shank 1 is generally in the form of a substantially circular cylindrical body, preferably pierced along its entire length. The screw shank 1 has a distal zone 3 whose end is provided with a chamfer 4 to facilitate penetration into a bone fragment, and whose outer portion is provided with a "bone" thread 5 of geometrical characteristics that may vary, but that are selected to facilitate good penetration into bone fragments and also good mechanical strength.

The screw shank 1 also has a proximal zone 7 having the same outside diameter as the distal zone 3 and carrying an outside thread 8 of a pitch selected to enable the screw head 2 to be mounted and displaced thereon. The end of the proximal zone 7 is provided with a collar 9 of diameter that is perceptibly greater than that of the unthreaded top portion 10 of the proximal zone 7, so as to form an abutment. The collar 9 is provided with two diametrically opposite slots 11 formed therein so as to enable the working portion of a tool (e.g. a screwdriver) to be inserted for the purpose of putting the screw shank 1 into place.

In accordance with the invention, the pitch of the distal thread 5 is identical to the pitch of the proximal thread 8, and said threads are also constant.

The screw head 2 of the invention is designed to be threaded onto the distal zone 3 of the screw shank 1 and to co-operate with its proximal zone 7. To this end, the screw head 2 is in the form of a substantially cylindrical body of revolution, and its outer generator lines impart a slightly frustoconical shape, said screw head 2 also having a through internal well provided with tapping 12. The tapping is complementary to the thread 8 of the proximal zone 7 so as to be suitable for screw engagement thereon. The tapping 12 likewise is of pitch identical to that of the thread 5 in the distal zone 3 so as to enable the screw head 2 to be threaded on and displaced along the distal zone by being turned. The screw head is also provided with two diametrically opposite slots 14 which are formed therein and that are open to the top of the head.

Consequently, such an assembly enables the screw head 2 to be engaged only via the distal zone 3 and by being turned on the thread 5 so as to make it possible subsequently to engage the screw head 2 onto the proximal thread 8 and come into abutment against the collar 9. Such a disposition prevents the user from taking the screw assembly of the invention apart easily.

Advantageously, the slots 14 of the screw head 2 and the slots 11 of the collar 9 come into alignment when the screw head is in abutment against the collar 9. To this end, the first thread of the thread 8 is angularly positioned relative to the slots 11. Similarly, the first thread of the tapping 12 is angularly positioned relative to the slots 14 and relative to the first thread of the thread 8.

The screw head 2 of the invention also includes an outside thread 13 in a manner that is well known in the prior art, which thread preferably extends over its entire length and is at a pitch that is smaller than its inside pitch 12. The outside thread 13 is thus also of a pitch smaller than the threads 5 and 8 located respectively in the distal and the proximal zones 3 and 7.

In accordance with the invention, the distal zone 3 and the proximal zone 7 are spaced apart by a central zone 15 shaped to be inactive while the screw of the invention is being turned so as to form a sliding zone for the bone fragments that are to be united and put into compression.

In a particularly advantageous version of the invention, as shown in FIGS. 1 and 2, the central zone 15 is formed by a zone that has no thread, and preferably by a zone that is substantially cylindrical and substantially smooth. By means of this configuration, the two bone fragments to be united and pressed against each other can thus move freely towards each other without being subjected to any interface that might limit or brake their movement.

As can be seen more particularly in FIGS. 1 and 2, the central zone 15 is thus in the form of a smooth cylindrical portion of diameter smaller than the outside diameter of the threads 5A and 8A making up the thread in the distal and proximal zones 3 and 7.

According to another particularly advantageous characteristic of the invention, the central zone 15 extends over a length that varies depending on the overall length of the screw shank 1, and preferably constitutes 27% to 60% of the total length of the screw shank 1. As described above, the threads 5 and 8 in the distal and proximal zones 3 and 7 have the same pitch. Nevertheless, according to an advantageous characteristic of the invention, the threads 5 and 8 can advantageously be of differing profiles.

This variation in screw thread profiles serves specifically to adapt each thread to its main function, without putting constraints on free passage of the screw head 2 since the pitches of the threads 5 and 8 remain equal.

Thus, in accordance with the invention, it is particularly advantageous to have the thread 5 in the distal zone 3 made up of threads 5A that slope to a greater extent than the threads 8 in the proximal zone 7.

Figure 3:
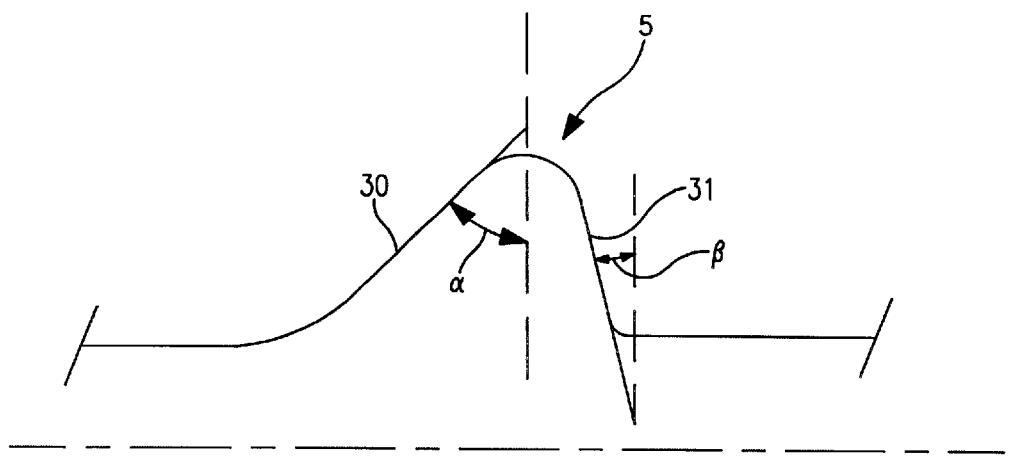
FIGS. 3 and 4 are diagrammatic fragmentary views showing the preferred geometrical shapes respectively for the threads of the distal portion and of the proximal portion of a compression osteosynthesis screw of the invention.
Figure 4:
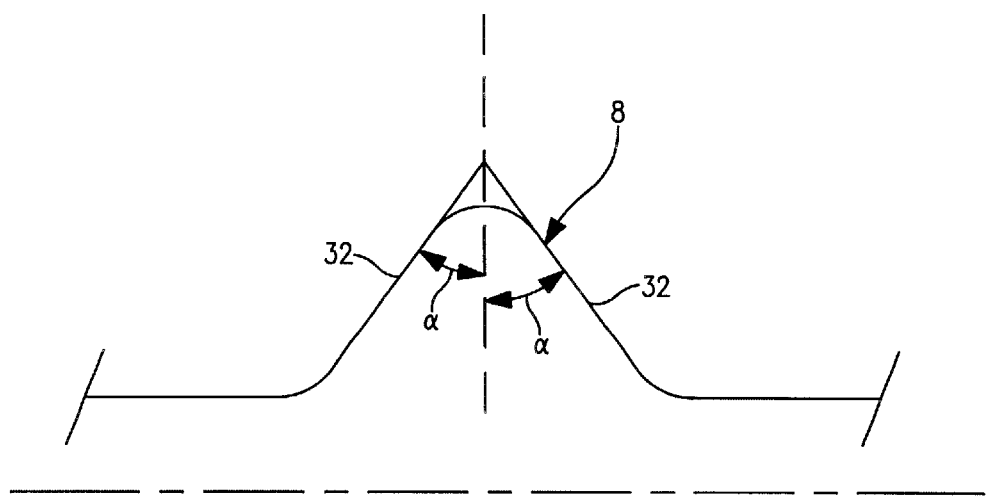

Advantageously, the thread of the distal zone 5 is a bone thread having sloping flanks (FIG. 3). By way of preferred example, the slope of the leading flank 30 of the thread 5 is, for example, 20°–40°, preferably 25°–35°, more preferably about 30° (angle α) relative to the vertical while the slope of its trailing flank 31 is, for example, 1°–10°, preferably 2°–4°, more preferably about 3°(angle β). This configuration makes it possible to obtain excellent strength for the screw shank while minimizing any evacuation of bone debris, thereby reducing potential phenomena of bone resorption.

Advantageously, the thread 8 of the proximal zone 7 is formed by isometric threads having flanks 32 both of which form an angle γ of, for example, 20°–40°, preferably 25°–35°, more preferably about 30° relative to the vertical. By means of this implementation, it is particularly easy to move the screw head 2 along the thread 8.

Figure 5:
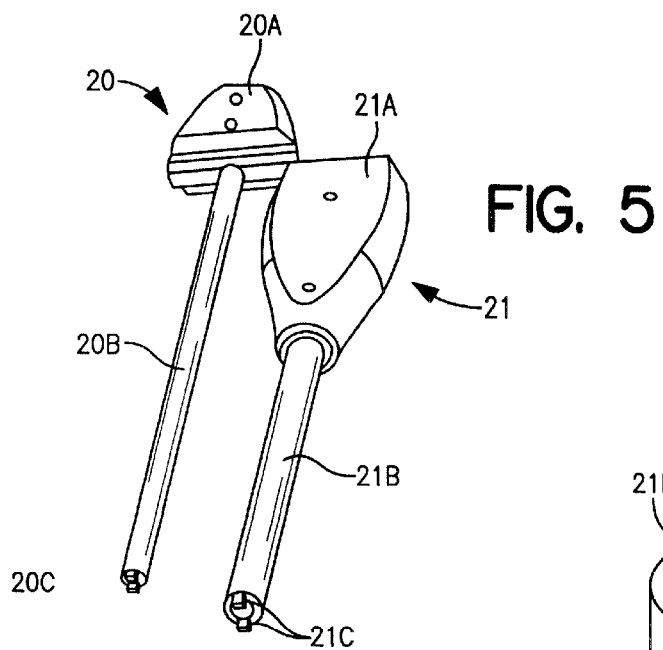
FIG. 5 is a general perspective view showing an ancillary device of the invention, with the two instruments that make it up being shown in a position where they are separate from each other.
Figure 6:
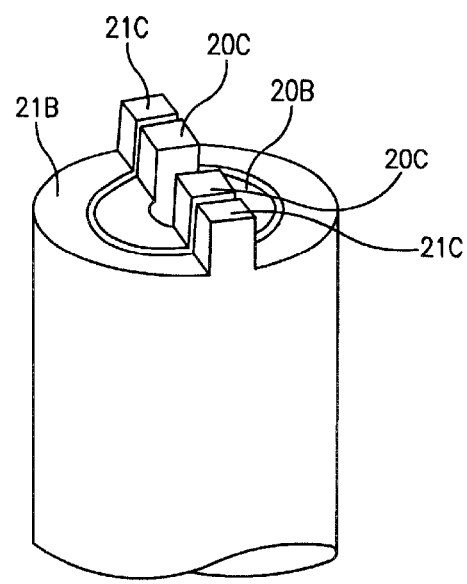
FIG. 6 is a fragmentary perspective view showing a detail of the working end of an ancillary device of the invention when the two instruments that make it up are engaged one in the other.
Figure 7:
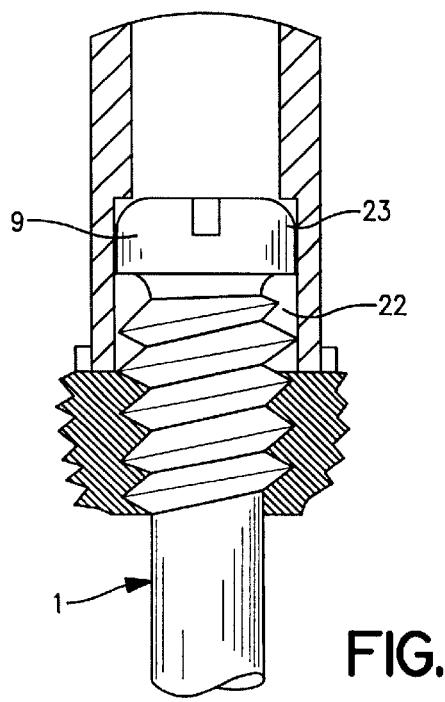
FIG. 7 is a fragmentary longitudinal section view of the ancillary device for turning the screw head, showing the abutment position of said element.

As shown in particular in FIGS. 5 to 7, the invention also provides a novel set of instruments for use with the osteosynthesis screw of the invention. In accordance with the invention and as shown in FIG. 5, the instruments for use with the osteosynthesis screw comprise in association, a set of two screwdrivers 20 and 21 forming respectively a first screwdriver 20 for turning the screw shank 1 and a second screwdriver 21 for turning the screw head 2. Each screwdriver 20, 21 comprises a respective handle 20A, 21A enabling the screwdriver to be held in the hand for turning purposes. Each handle 20A, 21A is secured to a hollow rod 20B, 21B engaged in the corresponding handle 20A, 21A. The working end of each rod 20B, 21B is provided with two diametrically opposite studs 20C, 21C of the same height and constituting the drive bits of each screwdriver.

The diameter of the rod 20B of the first screwdriver is smaller than the diameter of the rod 21B of the second screwdriver 21 so as to enable the first screwdriver 20 to be engaged axially inside the second screwdriver, as shown in particular in FIG. 6. The handles 20A and 21A are likewise shaped so as to be capable of being engaged one relative to the other so as to form a single handle for obtaining a single separable screwdriver instrument, depending on the intended use.

Advantageously, when the screwdrivers are assembled one in the other, the studs 20C and 21C of the rods 20B and 20C are in register with one another (FIG. 6).

In accordance with the invention, and as shown in FIG. 7, the second screwdriver 21 is provided at its working end portion with an internal setback 22 designed to receive the collar 9 on the screw shank 1 so that it comes into abutment against the end 23 of the setback, which setback is of dimensions that match those of the screw shank 1.

Thus, in accordance with the invention, the internal setback 22 is of a depth such that when the collar 9 comes into abutment against its end 23 while the screw head 2 is being turned, further turning is automatically prevented before the last turn of the thread 8 is reached so as to ensure that the screw head 2 does not escape from said thread 8. This design feature is particularly useful since it makes it possible to ensure that the screw does not become separated from its screw head during installation. In a particular advantageous version of the invention, the inside height of the setback 22 is such that turning of the screw head 2 is interrupted automatically and there is no possibility of subsequent translation movement of the screw head 2 once it is engaged with the thread 8 over the full length of its internal tapping, the respective bottom last turns of the screw head 2 and of the thread 8 preferably then being mutually engaged. This is specifically the position that is shown in FIG. 7, and it serves to retain maximum stability for the screw head 2 since its entire tapping 12 is engaged on the thread 8.

According to the invention, during installation, both screwdrivers 20 and 21 turn together initially (FIG. 6) for the purpose of turning both the screw shank 1 and the screw head 2 until the screw head has been completely buried. Thereafter, the inner screwdriver 20 is withdrawn so that only the outer screwdriver 21 can turn the screw head 2 along the screw shank 1. Under such circumstances, the internal setback 22 prevents the screw head 2 from going beyond the threaded zone, as represented by the thread 8, with the collar 9 coming into abutment against the end 23 of the setback automatically stopping further progress of the screw head 2.

The compression osteosynthesis screw of the invention operates as follows.

The shank 1 and the head 2 of the screw are delivered ready-assembled, i.e. in the configuration shown in FIG. 2, and the screw shank 1 is inserted by using an appropriate tool to drive it into the first bone fragment for piercing. Rotation of the screw shank 1 enables its distal zone 3 to pass through the first bone fragment and then also through the second bone fragment. Since the pitches of the threads 5A and 8A are identical, the two bone fragments to be united retain a relative position that does not change during this initial penetration stage. Once the screw head 2 begins to penetrate into the first bone portion via its outside thread 13, the two bone fragments to be united begin to come together because of the smaller pitch of said thread 13 as compared with the threads 5 and 8. This gives rise not only to the two bone fragments coming together, but also to them being put under compression. During this compression, the presence of the central zone 15 that has no interface relationship with the two bone fragments which meet around it via the break line, provides great freedom of positioning and sliding between the two bone fragments. No interfering friction action occurs in the central zone 15, thus making it possible to significantly increase the relative compression between the two bone fragments to be united and set.

Thereafter, a second compression stage can be performed by using a special ancillary tool to rotate the screw head 2 on its own, i.e. independently of the screw shank 1. Under such circumstances, the existence of an isometric thread 8 provides excellent control, good progress, and good stability for the screw head on the screw shank, thus ensuring good control over progress and compression.

By way of example, the length of the distal zone 3 may be, for example, 10 mm–30 mm, preferably about 15 mm (having 5–15 turns, preferably at least eight turns) so as to provide good anchoring in bone, the overall length of the screw head 2 can be, for example, 5 mm–15 mm, preferably about 8 mm so as to be capable of progressing by, for example, 5 mm–20 mm, preferably 6 mm in the bone, the length of the central zone 15 can lie in the range of, for example, 10 mm–70 mm, preferably about 11 mm to 52 mm, and the length of the proximal zone 7 can be, for example, 5 mm–20 mm, preferably about 14 mm.

The entire disclosure of all applications, patents and publications, cited above, and of corresponding French Patent Application No. 99 05399, filed Apr. 22, 1999, is hereby incorporated by reference.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. An osteosynthesis screw for applying compression to bone fragments, the screw comprising:

a screw shank having a thread with a distal zone and a proximal zone, and a screw head for threading on said screw shank and for co-operating with said proximal zone via internal tapping complementary to the thread of said shank, said screw head having an outside thread at a pitch that is smaller than the pitch of the thread of said screw shank, wherein said distal zone and said proximal zone are separated by a central zone, shaped to be inactive during screwing, to form a sliding zone for putting bone fragments into compression.

2. An osteosynthesis screw according to claim 1, wherein said central zone is formed by a zone having no thread.

3. An osteosynthesis screw according to claim 1, wherein said central zone is formed by a zone whose surface is substantially smooth.

4. An osteosynthesis screw according to claim 1, wherein said central zone extends over a length representing 27% to 60% of the total length of said screw shank.

5. An osteosynthesis screw according to claim 1, wherein the thread on said distal zone and the thread on said proximal zone are equal in pitch but different in profile.

6. An osteosynthesis screw according to claim 5, wherein the thread on said distal zone slopes more steeply than the thread on said proximal zone.

7. An osteosynthesis screw according to claim 5, wherein the thread on said distal zone is a bone thread having sloping flanks.

8. An osteosynthesis screw according to claim 7, wherein the slope of the flanks of the thread of said distal zone, relative to the vertical, is about 30° for the leading flank and about 3° for the trailing flank.

9. An osteosynthesis screw according to claim 1, wherein said internal tapping has a pitch identical to that of the thread of said distal zone so as to enable the screw head to be threaded thereon and to be moved thereover by being turned.

10. An osteosynthesis screw according to claim 1, wherein said proximal zone is provided with a collar against which the screw head is designed to come into abutment, the collar and the screw head each having a respective pair of diametrically opposite slots.

11. An osteosynthesis screw according to claim 10, wherein said slots of said collar and said screw head are in alignment when the screw head is in abutment against the collar.

12. An osteosynthesis screw according to claim 5, wherein the thread of said proximal zone is formed by isometric threads whose flanks form an angle of about 30° relative to the vertical.

13. An osteosynthesis screw according to claim 1, wherein the pitch of the thread on said distal zone is the same as the pitch of the thread on said proximal zone.

14. An osteosynthesis screw according to claim 13, wherein the thread on said distal zone and the thread on said proximal zone are both constant.

15. An osteosynthesis screw according to claim 1, wherein the thread of said proximal zone is formed of isometric threads.

16. A combination apparatus comprising an osteosynthesis screw according to claim 1, and an ancillary device, said ancillary device comprising:
    a first screwdriver designed for screwing the screw shank and a second screwdriver designed for turning the screw head,
    said first screwdriver being engaged axially inside the second screwdriver to enable the screw shank and the screw head to be turned simultaneously, and said first screw driver being separable therefrom to enable the screw head to be turned individually,
    said second screwdriver provided at its working end portion with an internal setback designed to receive a collar of the screw shank in an abutment position against an end of the setback, said setback being of a depth such that when the collar comes into abutment against its end while the screw head is being turned, further turning thereof is automatically blocked before a last turn of the proximal thread has been reached to prevent the screw head from escaping from said proximal thread.

17. An ancillary device according to claim 16, wherein the depth of the setback is such that turning of the screw head is interrupted automatically while all of the tapping is engaged on the proximal thread.

18. In a method of uniting bone fragments comprising bringing bone fragments together and putting said bone fragments under compression using an osteosynthesis screw, the improvement wherein said osteosynthesis screw comprises the osteosynthesis screw of claim 1.

* * * * *

UNITED STATES PATENT AND TRADEMARK OFFICE
CERTIFICATE OF CORRECTION

PATENT NO.    : 6,319,254 B1  
DATED         : November 20, 2001  
INVENTOR(S)   : Jean Christophe Alain Giet, Theo Jan Maria Knevels and Eric Stèphane Fourcault It is certified that error appears in the above-identified patent and that said Letters Patent is hereby corrected as shown below:

<u>Title page,</u>
Item [54], title, delete "Ancillaty" and insert therefor -- Ancillary --.

Signed and Sealed this

Fourth Day of June, 2002

Attest:

Attesting Officer

JAMES E. ROGAN
Director of the United States Patent and Trademark Office